(12) United States Patent
Fujita et al.

(10) Patent No.: US 8,131,030 B2
(45) Date of Patent: Mar. 6, 2012

(54) RECEIVING APPARATUS

(75) Inventors: Manabu Fujita, Hino (JP); Toshiaki Shigemori, Hachioji (JP); Seiichiro Kimoto, Hachioji (JP); Ayako Nagase, Hachioji (JP); Akira Matsui, Hino (JP); Kazutaka Nakatsuchi, Hino (JP)

(73) Assignee: Olympus Corporation, Tokyo (JP)

( * ) Notice: Subject to any disclaimer, the term of this patent is extended or adjusted under 35 U.S.C. 154(b) by 903 days.

(21) Appl. No.: 11/596,998

(22) PCT Filed: May 13, 2005

(86) PCT No.: PCT/JP2005/008805
§ 371 (c)(1),
(2), (4) Date: Jul. 15, 2008

(87) PCT Pub. No.: WO2005/115218
PCT Pub. Date: Dec. 8, 2005

(65) Prior Publication Data
US 2008/0267466 A1 Oct. 30, 2008

(30) Foreign Application Priority Data
May 25, 2004 (JP) .................. 2004-154375

(51) Int. Cl.
*G06K 9/00* (2006.01)
(52) U.S. Cl. ...................... 382/128; 600/109
(58) Field of Classification Search .............. 382/128; 600/109, 476; 348/222.1
See application file for complete search history.

(56) References Cited

U.S. PATENT DOCUMENTS

| 6,240,312 | B1 * | 5/2001 | Alfano et al. ............. 600/476 |
| 6,545,709 | B2 * | 4/2003 | Takei et al. ............. 348/222.1 |
| 6,764,440 | B2 * | 7/2004 | Iddan et al. ............. 600/109 |
| 6,855,111 | B2 * | 2/2005 | Yokoi et al. ............. 600/179 |
| 2002/0109779 | A1 | 8/2002 | Kuroiwa |
| 2002/0173718 | A1 | 11/2002 | Frisch et al. |
| 2003/0213495 | A1 | 11/2003 | Fujita et al. |
| 2004/0193010 | A1 | 9/2004 | Fujimori et al. |

FOREIGN PATENT DOCUMENTS

| JP | 2002-247518 | 8/2002 |
| JP | 2003-19111 | 1/2003 |
| JP | 2003-325439 | 11/2003 |
| JP | 2004-298241 | 10/2004 |

* cited by examiner

*Primary Examiner* — Louis Arana
(74) *Attorney, Agent, or Firm* — Scully, Scott, Murphy & Presser, P.C.

(57) ABSTRACT

Each of detecting circuits 36a, 36d, 36f, and 36h detects a key signal such as a horizontal synchronization signal, a vertical synchronization signal, a capsule ID, a WB coefficient, and error information, i.e., a key signal superposed on RF signals received by an RF receiving unit 33. Each of determining units 36b, 36c, 36e, 36g, and 36i determines whether an image is valid or invalid based on the result of detection. A recording deciding unit 36k decides whether to record the image information in a storage unit 35 or not based on the result of determination. Thus, a receiving apparatus 3 can stop recording the image information received when a trouble occurs, thereby preventing defective images from mixing into the recorded image information, and preventing a recorded image size from becoming large, whereby necessary images can be recorded within a predetermined examination time.

7 Claims, 4 Drawing Sheets

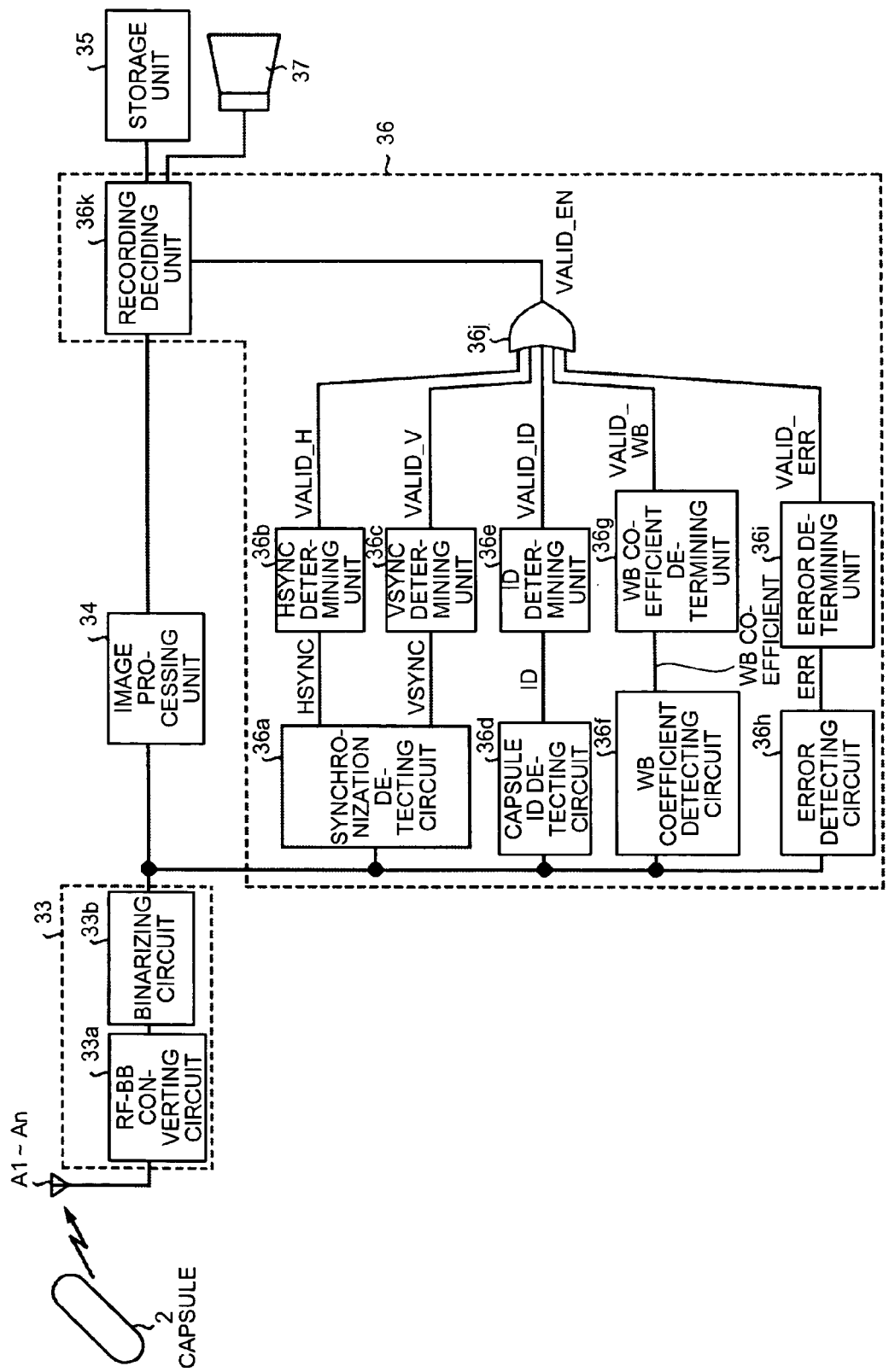

RECEIVING APPARATUS

TECHNICAL FIELD

The present invention relates to a receiving apparatus which employs plural antennas provided outside a subject body and receives radio image signals transmitted from a body-insertable device, such as a swallowable capsule endoscope, that is introduced into the subject body, and more particularly to a receiving apparatus which stops recording image information when there is a problem.

BACKGROUND ART

In recent years, a capsule endoscope having an imaging function and a radio communication function appears in a field of endoscope. After being swallowed by a patient, i.e., a subject, from the mouth for an observation (examination), the capsule endoscope travels through inside internal organs (body cavities) such as stomach and small intestine following peristaltic movements and sequentially captures images using the imaging function until naturally discharged from a living body (human body) of the subject, in other word, during an observation period.

During the observation period in which the capsule endoscope travels through the internal organs, the capsule endoscope captures images in the body cavities thereby obtaining image data, and sequentially transmits the image data to a receiving apparatus provided outside the subject body using the radio communication function. The image data received is accumulated in a memory inside the receiving apparatus. When the subject carries the receiving apparatus equipped with the radio communication function and the memory function, the subject can move freely without inconveniences even after swallowing the capsule endoscope and before discharging the same, i.e., even during the observation period. After the observation finishes, a doctor or a nurse can display images inside the body cavities on a display unit or the like based on the image data accumulated in the memory of the receiving apparatus, and make diagnosis.

Generally, the receiving apparatus includes plural antennas for receiving image signals transmitted from the capsule endoscope. The antennas are dispersedly arranged outside the subject body and one with a less error in image signal reception is selected for the reception via switching. For example, Patent Document 1 describes a receiver which selects one of plural antennas arranged outside the subject body by switching and locates a capsule endoscope, which sends image signals, inside the subject body based on strength of an electric field received by each antenna.

Patent Document 1: Japanese Patent Application Laid-Open No. 2003-19111

DISCLOSURE OF INVENTION

Problem to be Solved by the Invention

The above mentioned receiver, however, records all the image information received in the form of radio signals in a recording medium even when high resolution images captured by the capsule endoscope to be recorded in the recording medium include defective images. The defective images tend to be image information of high frequency band. Therefore, when the received defective image is compressed through image processing, a size of the image to be recorded tends to become large and compression cannot be performed to a high degree. Then, necessary recording cannot be finished within a predetermined examination time (10 hours, for example). Further, when the defective image is present within the recorded images in the recording medium, reproduction of the images may take a long time, or later processing such as image processing or deletion of the defective image in a workstation, which displays the images recorded in the recording medium, may become burdensome. Further, the subject can carry the receiver while moving freely, and may not notice an interruption of communication even when the receiver becomes unable to perform radio communication for a long time period during the radio communication of the image signals, and may carry on with the examination. Then, the subject may need to undergo the examination all over again after a predetermined time for the examination passes.

The present invention is achieved in view of the foregoing, and an object of the present invention is to provide a receiving apparatus which can prevent the defective image from mixing into image information by stopping the recording of the image information received by the receiving apparatus when there is a trouble, and which can finish recording of necessary images within a predetermined examination time by preventing an excessive increase in the recorded image size.

Means for Solving Problem

In order to solve the problems as described above and to achieve an object, a receiving apparatus according to one aspect of the present invention can be carried by a subject and which receives radio signals transmitted from a body-insertable device traveling inside the subject, and includes a recording unit which records image information as the received radio signal; a detector which detects a key signal contained in the received radio signal; and a recording controller which stops recording of the received image information into the recording unit based on a result of detection by the detector.

The receiving apparatus may further include a warning unit which raises an alarm when the key signal is detected by the detector continuously for a predetermined time period.

In the receiving apparatus the key signal detected by the detector may include at least one of a synchronization signal which is superposed on the radio signal and employed for the image information, an identification signal which is superposed on the radio signal and serves for identification of the body-insertable device, a white balance coefficient signal which is superposed on the radio signal and employed for adjusting white balance of the image information, and error information employed for error correction of the radio signal.

In the receiving apparatus the recording controller may stop recording the received image information into the recording unit when the detector does not detect the synchronization signal.

In the receiving apparatus the recording controller may stop recording the received image information into the recording unit when the identification signal detected by the detector is not identical with an identification signal set in advance.

In the receiving apparatus the recording controller may stop recording the received image information into the recording unit when the white balance coefficient signal detected by the detector is not identical with an expected value set in advance or is out of a predetermined range.

In the receiving apparatus the detector may detect the error information in a predetermined image region, and the recording controller stops recording the received image information into the recording unit when an error number of the error information detected by the detector is larger than a number set in advance.

EFFECT OF THE INVENTION

The receiving apparatus according to the present invention, on recording the image information as the radio signal in the recording unit, detects the key signal contained in the radio signal by the detector, and stops the recording of the image information into the recording unit by the record controller based on the results of detection, whereby the recording of the image information received by the receiving apparatus can be stopped when there is a problem, and the defective images are prevented from mixing into the image information, and at the same time, the excessive increase in the recorded image size can be prevented and the recording of the necessary images can be finished within the predetermined examination time.

BRIEF DESCRIPTION OF DRAWINGS

FIG. 4 is a block diagram of a structure of a detecting/determining unit according to the first embodiment as shown in FIG. 3.

EXPLANATIONS OF LETTERS OR NUMERALS

Figure 1:
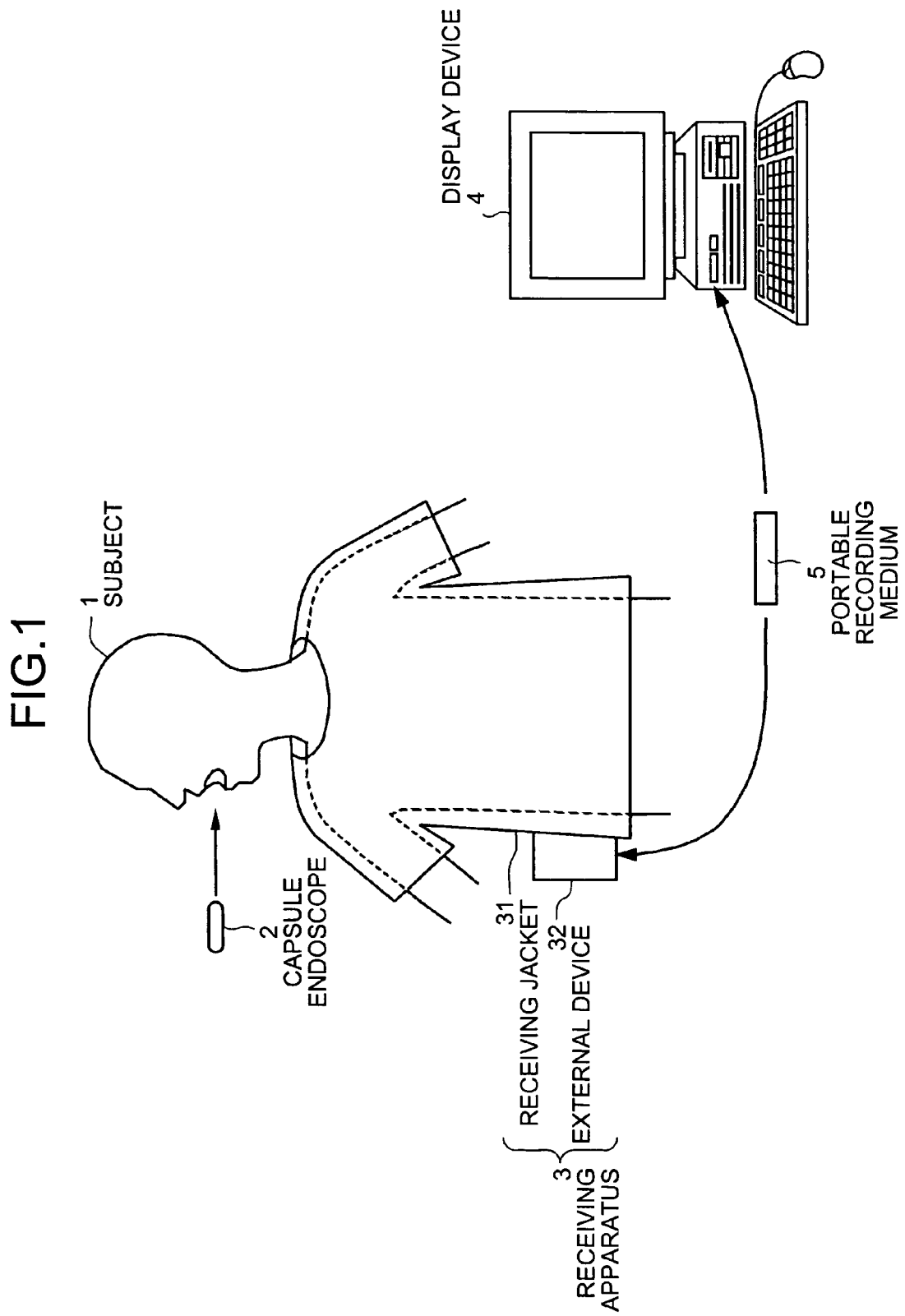
FIG. 1 is a schematic diagram of an overall structure of a wireless intra-subject information acquiring system which includes a body-insertable device according to a first embodiment.

1 Subject
2 Capsule endoscope
3 Receiving apparatus
4 Display device
5 Portable recording medium
20 LED
21 LED driving circuit
22 Imaging unit
23 CCD
24 CCD driving circuit
25 Signal processing circuit
26 Imaging timing generation circuit
27 RF transmitting unit
28 Transmitting antenna unit
29 System control circuit
30 Battery
31 Receiving jacket
32 External device
33 RF receiving unit
33a RF-BB converting circuit
33b Binarizing circuit
34 Image processing unit
35 Storage unit
36 Detecting/determining unit
36a Synchronization detecting circuit
36b HSYNC determining unit
36c VSYNC determining unit
36d Capsule ID detecting circuit
36e ID determining unit
36f WB coefficient detecting circuit
36g WB coefficient determining unit
36h Error detecting circuit
36i Error number determining unit
36j OR circuit
36k Recording deciding unit
37 Warning unit
38 Power supply unit
A1 to An Receiving antenna

BEST MODE(S) FOR CARRYING OUT THE INVENTION

Exemplary embodiments of a receiving apparatus according to the present invention will be described in detail below with reference to the accompanying drawings of FIGS. 1 to 4. It should be noted that the present invention is not limited to the embodiments and that various modifications can be made without departing from the scope of the present invention.

First Embodiment

FIG. 1 is a schematic diagram of an overall structure of a wireless intra-subject information acquiring system which includes a body-insertable device according to a first embodiment. A capsule endoscope will be described below as an example of the body-insertable device of the wireless intra-subject information acquiring system. In FIG. 1, the wireless intra-subject information acquiring system includes a receiving apparatus 3 which has a radio reception function, and a capsule endoscope (body-insertable device) 2 which is introduced into a subject body 1, captures images inside body cavities, and transmits data such as an image signal to the receiving apparatus 3. Further, the wireless intra-subject information acquiring system includes a display device 4 which displays images inside the body cavities based on the image signals received by the receiving apparatus 3, and a portable recording medium 5 which serves for data transfer between the receiving apparatus 3 and the display device 4. The receiving apparatus 3 includes a receiving jacket 31 which is worn by the subject 1, and an external device 32 which performs, for example, processing on received radio signals.

Figure 2:
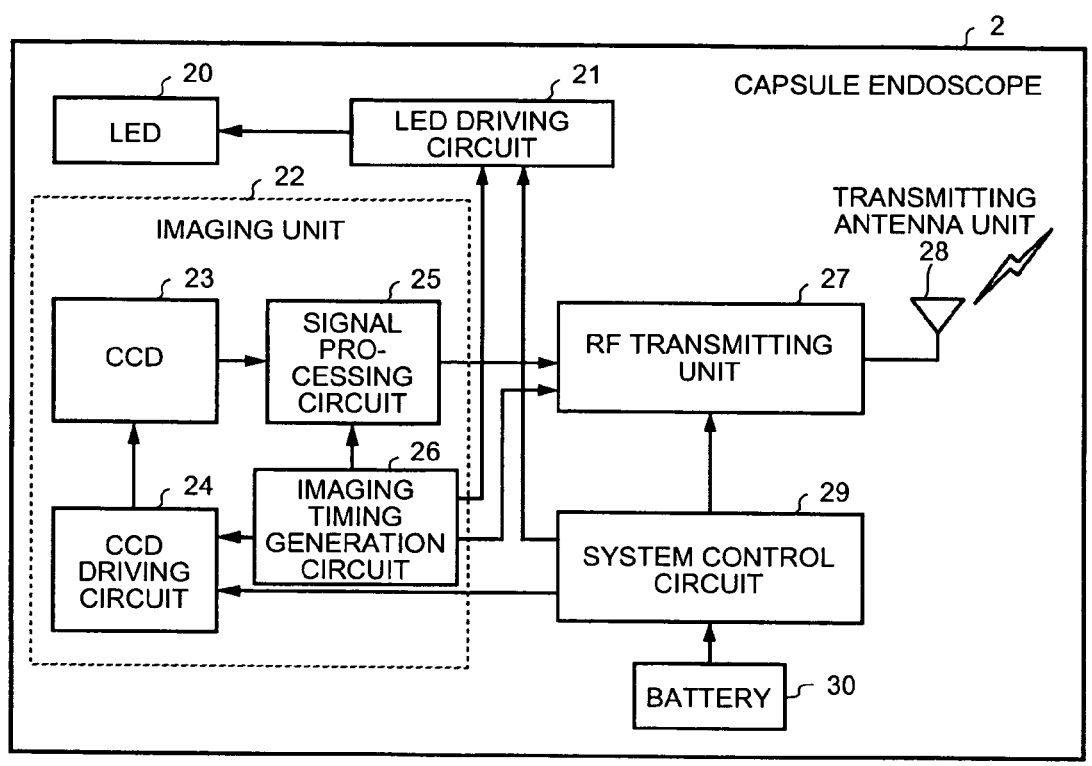
FIG. 2 is a block diagram of an internal structure of a capsule endoscope according to the first embodiment as shown in FIG. 1.

The capsule endoscope 2 includes, as shown in the block diagram of FIG. 2, a light emitting diode (LED) 20 which is an illuminator for illuminating an examined area in a body cavity of the subject 1, an LED driving circuit 21 which controls a driven state of the LED 20, a Charge Coupled Device (CCD) 23 which is an imager that captures images inside the body cavity as reflected light from an area illuminated by the LED 20, a CCD driving circuit 24 which controls a driven state of the CCD 23, a signal processing circuit 25 which processes image signals supplied from the CCD 23 into image information of a desired format, and an imaging timing generation circuit 26 which is a clock generator that outputs a reference clock to define driving timing such as illuminating timing of the LED 20 and imaging timing of the CCD 23. Further, the capsule endoscope 2 includes an RF transmitting unit 27 which modulates the image information obtained via the image capturing into RF signals, and a transmitting antenna unit 28 which is a radio transmitter that radio transmits the RF signals supplied from the RF transmitting unit 27. The capsule endoscope 2 further includes a system control circuit 29 which controls operations of the LED driving circuit 21, the CCD driving circuit 24, and the RF transmitting unit 27, and a battery 30 which supplies power to the aforementioned electric devices. In the description, the CCD 23, the CCD driving circuit 24, the signal processing circuit 25, and the imaging timing generation circuit 26 are referred collectively as an imaging unit 22.

The capsule endoscope 2, having the above mentioned structure, operates so as to obtain image signals of the examined area illuminated by the LED 20 using the CCD 23 based on a reference clock which sets desired imaging timing, while the capsule endoscope 2 is inside the subject body 1. Based on the reference clock, analog image signals obtained are subjected to signal processing in the signal processing circuit 25, and a key signal described later is superposed on the processed signal, and the resulting signal is converted into an RF signal, and thereafter the resulting signal is transmitted to an outside of the subject body 1 via the transmitting antenna unit 28.

The display device 4 serves to display images inside body cavities obtained by the capsule endoscope 2, and has a structure like a workstation that displays images based on data obtained from the portable recording medium 5. Specifically, the display device 4 may directly display images as in a cathode ray tube (CRT) display and a liquid crystal display. Alternatively, the display device 4 may output images onto other media as in a printer.

The portable recording medium 5 can be attached to and detached from the external device 32 and the display device 4, and information can be retrieved from or recorded into the portable recording medium 5 while the portable recording medium 5 is attached to the external device 32 and the display device 4. In the first embodiment, the portable recording medium 5 is attached to the external device 32 and records data transmitted from the capsule endoscope 2 while the capsule endoscope travels in the body cavities of the subject body 1. After the capsule endoscope 2 is discharged from the subject body 1, in other words, after the imaging inside the subject body 1 is finished, the portable recording medium 5 is removed from the external device 32 and attached to the display device 4, then the display device 4 reads out the data recorded in the portable recording medium 5. Since the portable recording medium 5 including a Compact Flash® memory or the like transfers data between the external device 32 and the display device 4, the subject 1 can move more freely during the imaging inside the body cavities compared with a time when the examination is carried out with a system including the external device 32 and the display device 4 directly connected by a cable. Here, the portable recording medium 5 is employed for data transfer between the external device 32 and the display device 4. A manner of data transfer, however, is not limited thereto. For example, the external device 32 may include other embedded type of recording device, such as a hard disk, and may be connected to the display device 4 by a cable or by radio for data transfer.

Figure 3:
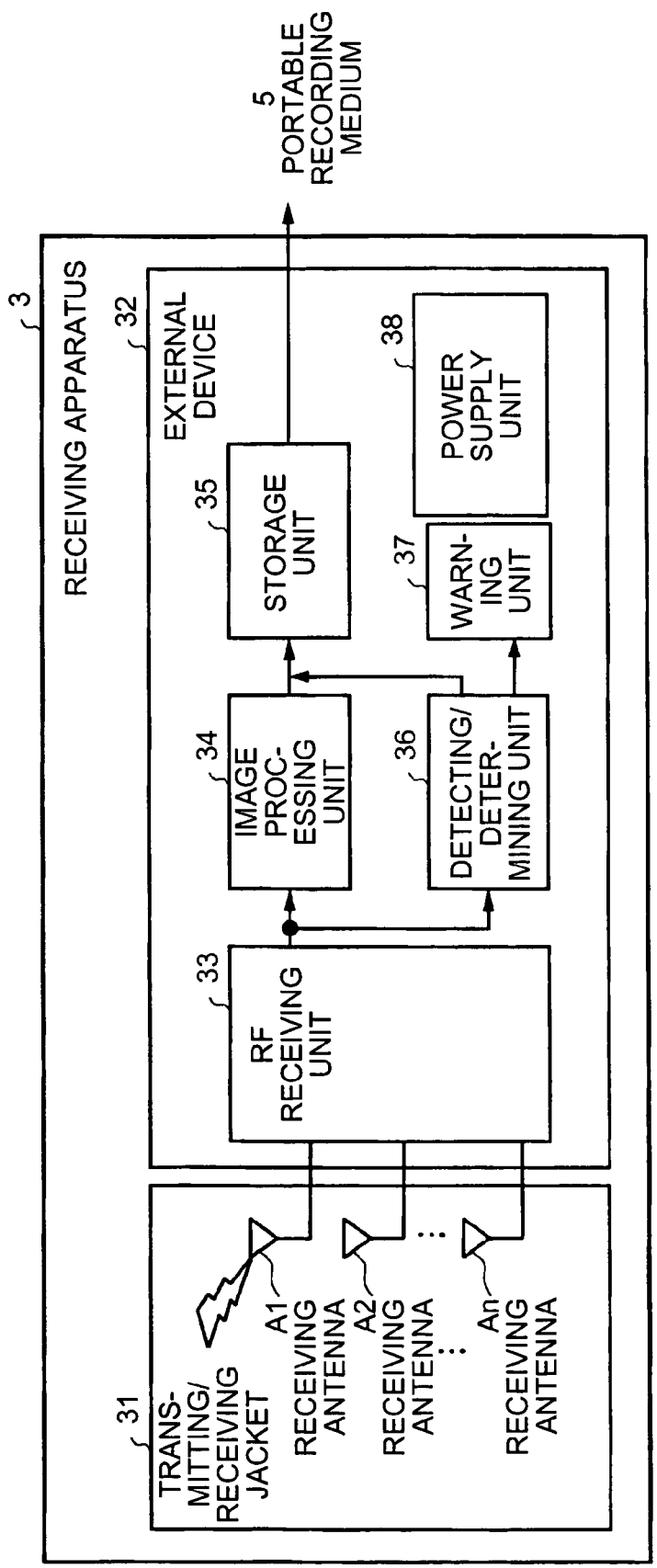
FIG. 3 is a block diagram of an internal structure of a receiving apparatus according to the first embodiment as shown in FIG. 1.

A structure of the receiving apparatus will be described with reference to the block diagram of FIG. 3. The receiving apparatus 3 has a function of receiving image information of an interior of body cavities when the image information is transmitted from the capsule endoscope 2 by radio. As shown in FIG. 3, the receiving apparatus 3 is formed so as to be worn by the subject 1, and includes the receiving jacket 31 provided with receiving antennas A1 to An, and the external device 32 which performs, for example, processing of radio signals received by the receiving jacket 31. The receiving antennas A1 to An may be directly attached onto an outer surface of the subject body 1, rather than being attached to the receiving jacket 31. The receiving antennas A1 to An may be detachable from the receiving jacket 31.

The external device 32 includes an RF receiving unit 33 which performs predetermined signal processing such as demodulation on the radio signals received by the receiving antennas A1 to An and extracts image information acquired by the capsule endoscope 2 from the radio signals, an image processing unit 34 which performs necessary image processing on the extracted image information, and a storage unit 35 which works as a recording unit for recording the image information after the image processing. Thus, the external device 32 performs signal processing of the radio signals transmitted from the capsule endoscope 2. In the first embodiment, the RF receiving unit 33 includes, as shown in FIG. 4, an RF-BB converting circuit 33a which converts RF signals into baseband signals, and a binarizing circuit 33b which performs processing such as amplification and frequency band filtering of baseband signals whose signal level is very low and changes the signal level to a level processible in a later stage. The image information is recorded into the portable recording medium 5 via the image processing unit 34 and the storage unit 35.

Further, the external device 32 includes a detecting/determining unit 36 which works as a detecting unit that detects the key signals superposed on the radio signals (RF signals) as well as a recording controlling unit that determines whether to record the received image information in the storage unit 35 or not based on the results of detection, and a warning unit 37 which works as a warning unit that raises alarm. The key signals transmitted from the capsule endoscope 2 includes, for example, a horizontal synchronization signal (HSYNC) and a vertical synchronization signal (VSYNC) for synchronizing the image information, a capsule ID which is identification information of the capsule endoscope, a White Balance (WB) coefficient signal which is employed to adjust White Balance (hereinafter denoted as WB) of the image information, and error information, such as parity information for parity check, of a predetermined image region.

The detecting/determining unit 36, as shown in the block diagram of FIG. 4, includes a synchronization detecting circuit 36a which detects the horizontal synchronization signal (HSYNC) and the vertical synchronization signal (VSYNC) as the key signal, an HSYNC determining unit 36b which determines whether the image is valid or invalid based on the result of detection of the horizontal synchronization signal in the synchronization detecting circuit 36a, a VSYNC determining unit 36c which determines whether the image is valid or invalid based on the result of detection of the vertical synchronization signal in the synchronization detecting circuit 36a, a capsule ID detecting circuit 36d which detects a capsule ID as the key signal, an ID determining unit 36e which determines whether the image is valid or invalid based on the result of detection of the capsule ID in the capsule ID detecting circuit 36d, a WB coefficient detecting circuit 36f which detects a WB coefficient as the key signal, a WB coefficient determining unit 36g which determines whether the image is valid or invalid based on the result of detection in the WB coefficient detecting circuit 36f, an error detecting circuit 36h which detects error information as the key signal, and an error determining unit 36i which determines whether the image is valid or invalid based on the result of detection in the error detecting circuit 36h.

Specifically, the HSYNC determining unit 36b outputs a parameter value indicating validity of the image determining that the image is valid when the number of the horizontal synchronization signals detected within one frame, one field, or a predetermined image region by the synchronization detecting circuit 36a is not less than threshold n, whereas the HSYNC determining unit 36b outputs a parameter value indicating invalidity of the image determining that the image is invalid when the number of the detected-horizontal synchronization signals is less than n. The threshold n can be set to any value as a parameter. The VSYNC determining unit 36c outputs a parameter value indicating validity of the image determining that the image is valid when the synchronization detecting circuit 36a detects the vertical synchronization signal, whereas the VSYNC determining unit 36c outputs a parameter value indicating invalidity of the image determining that the image is invalid when the synchronization detecting circuit 36a does not detect the vertical synchronization signal.

In the ID determining unit 36e, the capsule ID which is an identification signal of the capsule endoscope 2 is registered in advance. For example, information of the capsule ID is supplied from the display device 4 which is a workstation before the examination starts. The ID determining unit 36e determines whether the capsule ID detected by the capsule ID detecting circuit 36d is identical with the registered capsule ID or not. When two capsule IDs are identical, the detected capsule endoscope 2 is a relevant one, and hence the ID determining unit 36e outputs a parameter value indicating validity of the image determining that the received frame contains a valid image. On the other hand, when two capsule IDs are not identical, the detected capsule endoscope 2 is not a relevant one, and hence, the ID determining unit 36e outputs a parameter value indicating invalidity of the image determining that the received frame contains an invalid image.

In the WB coefficient determining unit 36g, information on a WB coefficient of the capsule endoscope 2 is registered in advance. For example, the information on the WB coefficient is supplied from the display device 4 and registered before the examination starts similarly to the process in the ID determining unit 36e. The WB coefficient determining unit 36g outputs a parameter value indicating validity determining that the received frame contains a valid image when the WB coefficient detected by the WB coefficient detecting circuit 36f is identical to the registered WB coefficient or within a predetermined range, because when the WB coefficient is within such a range, there is no negative influence on white balance adjustment. On the other hand, the WB coefficient determining unit 36g outputs a parameter value indicating invalidity determining that the received frame contains an invalid image when the WB coefficient detected by the WB coefficient detecting circuit 36f is not identical with the registered WB coefficient or not within the predetermined range, because when the WB coefficient is not within such a range, the white balance adjustment cannot be performed well.

In the error detecting circuit 36h, the number of communication errors (error number) which may occur during the radio communication is set as a threshold in advance based on an input from the display device 4 before, for example, the examination starts. When the error number within a one-frame image region is smaller than the set threshold, the error detecting circuit 36h determines that a necessary image for the examination has been received and that the received frame is a valid image, and outputs a parameter value indicating validity. On the other hand, when the error number is larger than the set threshold, the error detecting circuit 36h determines that a necessary image for the examination has not been received and that the received frame is an invalid image, and outputs a parameter value indicating invalidity. The parameter value indicating validity consists of low level signals, for example, whereas the parameter value indicating invalidity consists of high level signals whose level is higher than the level of the signals indicating validity, for example. The key signals (capsule ID, WB coefficient, and the like) to be sent to the receiving apparatus 3 can be checked in advance through the inputs from the workstation as described above. Alternatively, the capsule endoscope 2 to be employed in the examination may be brought close to the receiving antennas A1 to An for a predetermined time period so that the receiving antennas A1 to An receive the capsule ID and the WB coefficient transmitted from the capsule endoscope 2. Thus, the ID determining unit 36e and the WB coefficient determining unit 36g may be able to recognize the key signals.

The detecting/determining unit 36 includes an OR circuit 36j to which the parameter values indicating validity/invalidity as described above are supplied, and a recording deciding unit 36k which decides whether to record the image information supplied from the image processing unit 34 or not according to the output from the OR circuit 36j. The OR circuit 36j outputs a high level signal indicating invalidity of the image to the recording deciding unit 36k when at least one of the signals supplied from the determining units 36, 36c, 36e, 36g, and 36i is a parameter value indicating invalidity, whereas the OR circuit 36j outputs a low level signal indicating validity of the image to the recording deciding unit 36k when all of the signals supplied from the determining units 36, 36c, 36e, 36g, and 36i are parameter values indicating validity.

The recording deciding unit 36k decides whether to record the image information of the predetermined image region or not according to the level of the signal supplied from the OR circuit 36j. The recording deciding unit 36k determines that the image is invalid when the supplied signal is high level, and stops recording of the image information supplied from the image processing unit 34 into the storage unit 35, whereas the recording deciding unit 36k determines that the image is valid when the supplied signal is low level, and permits recording of the image information supplied from the image processing unit 34 into the storage unit 35. The recording deciding unit 36k monitors duration time of the low level signals among the signals supplied from the OR circuit 36j. When the duration time reaches a predetermined time period, the recording deciding unit 36k determines that the valid image necessary for the examination has not been obtained, and drive controls the warning unit 37, which is a warning unit, so that the warning unit 37 raise a predetermined alarm.

The warning unit 37 is configured to raise the predetermined alarm. A warning can be given, for example, by generating a warning sound by a buzzer, making a display by lighting or blinking of an LED, generating vibrations by a vibrator, or generating heat by a heater. Other than those, the warning can be given in any manners as far as it can be sensed by five senses of a human. The external device 32 further includes a power supply unit 38 which is provided with a predetermined battery or an AC power adapter.

Each element of the external device 32 uses the power supplied from the power supply unit 38 as driving energy.

Thus, according to the embodiment, the detecting circuit detects each of the key signals, which include the synchronization signal, the capsule ID signal, the WB coefficient signal, and the error information, and which are superposed on the RF signal received by the RF receiving unit, and each determining unit determines whether the image is valid or invalid based on the results of detection, and further the recording deciding unit decides whether to record the received image information in the storage unit or not based on the results of determination. Therefore, when a trouble occurs during the transmission of the RF signals, for example, the receiving apparatus stops recording the received image information in response to the occurrence of the trouble, whereby the receiving apparatus can prevent the defective images from mixing into the image information, and prevent the recorded image size from becoming too large, whereby the recording of necessary images can be performed within the predetermined examination time.

Further, in the embodiment, the recording deciding unit monitors the duration time of the signals which indicates the invalid images, and raises alarm when the duration time reaches the predetermined time period. Therefore, the subject can recognize trouble of the receiving apparatus based on the alarm, and take appropriate responses. For example, the subject can contact the doctor so that the image information can be properly obtained. Thus, frequency of re-examinations can be decreased.

The key signals are not limited to those described above according to the embodiment. For example, the intensity level of received RF signal supplied from the RF receiving unit, or the signal level (voltage level) of the image information supplied from the capsule endoscope may be employed as the key signals. In this case, a reference signal may be set corresponding to the key signal and compared with the received signal, whereby the validity/invalidity of the received image can be determined.

INDUSTRIAL APPLICABILITY

As can be seen from the foregoing, the body-insertable device according to the present invention is useful for a medical observation apparatus, such as the capsule endoscope, which is introduced into the human body for an observation of an examined area, and more particularly suitable for preventing the defective images from mixing into the recorded image information by stopping the recording of the image information received by the receiving apparatus when trouble occurs and for preventing the recorded image size from becoming large, so that the recording of the necessary images can be performed within the predetermined examination time.

The invention claimed is:

1. A receiving apparatus which can be carried by a subject and which receives a radio signal transmitted from a body-insertable device traveling inside the subject, the receiving apparatus comprising:
   a recording unit which records image information included in the received radio signal;
   a detector which detects a key signal contained in the received radio signal;
   a determining unit which determines whether the received image information is valid or invalid based on a result of detection by the detector; and
   a recording controller which stops recording of the received image information into the recording unit if the received image information is invalid.

2. The receiving apparatus according to claim 1, further comprising
   a warning unit which raises an alarm when the key signal is detected by the detector continuously for a predetermined time period.

3. The receiving apparatus according to claim 1, wherein the key signal detected by the detector includes at least one of a synchronization signal which is superposed on the radio signal and employed for the image information, an identification signal which is superposed on the radio signal and serves for identification of the body-insertable device, a white balance coefficient signal which is superposed on the radio signal and employed for adjusting white balance of the image information, and error information employed for error correction of the radio signal.

4. The receiving apparatus according to claim 3, wherein the recording controller stops recording the received image information into the recording unit when the detecting unit does not detect the synchronization signal.

5. The receiving apparatus according to claim 3, wherein the recording controller stops recording the received image information into the recording unit when the identification signal detected by the detector is not identical with an identification signal set in advance.

6. The receiving apparatus according to claim 3, wherein the recording controller stops recording the received image information into the recording unit when the white balance coefficient signal detected by the detector is not identical with an expected value set in advance or is out of a predetermined range.

7. The receiving apparatus according to claim 3, wherein the detector detects the error information in a predetermined image region, and
   the recording controller stops recording the received image information into the recording unit when an error number determined from the error information detected by the detector is larger than a number set in advance.

* * * * *